United States Patent [19]

Schumacher et al.

[11] 4,415,744
[45] Nov. 15, 1983

[54] VAPOR PHASE NITRATION OF AROMATIC COMPOUNDS

[75] Inventors: Ignatius Schumacher, Ballwin; Kang-Bo Wang, Creve Coeur, both of Mo.

[73] Assignee: Monsanto Company, St. Louis, Mo.

[21] Appl. No.: 313,522

[22] Filed: Oct. 21, 1981

[51] Int. Cl.$^3$ .............................................. C07C 79/46
[52] U.S. Cl. ..................... 560/20; 260/688; 562/434; 568/584; 568/929; 568/937; 568/939; 568/940; 502/237; 502/241; 502/243; 502/250; 502/255; 502/260
[58] Field of Search ......................... 260/688; 560/20; 562/434; 568/534, 929, 937, 939, 940

[56] References Cited

U.S. PATENT DOCUMENTS

| | | |
|---|---|---|
| 2,109,873 | 3/1938 | Wilhelm ............................ 568/939 |
| 2,431,585 | 11/1947 | Rout ................................. 568/939 |
| 3,966,830 | 6/1976 | Shimada et al. .................... 568/937 |
| 4,107,220 | 8/1978 | Owsley et al. ..................... 568/937 |
| 4,112,006 | 9/1978 | Schubert et al. ................... 568/940 |

OTHER PUBLICATIONS

McKee et al, Industrial and Engineering Chemistry, vol. 28, (1958), pp. 662–667.

Primary Examiner—Leland A. Sebastian
Attorney, Agent, or Firm—Wendell W. Brooks; James C. Logomasini; Arnold H. Cole

[57] ABSTRACT

Aromatic compounds are nitrated in the vapor phase via a process comprising contacting the aromatic compound with a nitrating agent in the presence of a nitration promotion catalyst which comprises the adduct of:
(a) an alumina-silica-metal oxide combination represented by the formula:

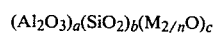

$$(Al_2O_3)_a(SiO_2)_b(M_{2/n}O)_c$$

wherein M is a metal cation selected from the group consisting of the lanthanides or rare earths, Groups 1b, 2b, 5b, 6b, 7b, and 8 of the Periodic Table of the Elements, and mixtures thereof, and a, b, and c represent weight percent of the $Al_2O_3$, $SiO_2$, and $M_{2/n}O$ components, respectively, in the alumina-silica-metal oxide combination, with a being 0 to 100, b being 0 to 100, and c being 0 to 50, and n represents an integer from 1 to 7 of the valence of the metal cation, with the proviso that the sum of (a+b) must be greater than 0, and
(b) a catalytically effective amount of sulfur trioxide.

45 Claims, No Drawings

VAPOR PHASE NITRATION OF AROMATIC COMPOUNDS

CROSS-REFERENCE TO RELATED APPLICATION

"Catalysts", Ser. No. 313,519, filed Oct. 21, 1981.

BACKGROUND OF THE INVENTION

1. Field of the Invention

This invention relates to a process for the vapor phase nitration of aromatic compounds. More particularly, this invention relates to a process for the vapor phase nitration of aromatic compounds in the presence of a nitration promoting catalyst which comprises the adduct of:

(a) an alumina-silica-metal oxide combination represented by the formula:

$$(Al_2O_3)_a(SiO_2)_b(M_{2/n}O)_c$$

wherein M is a metal cation selected from the group consisting of the lanthanides or rare earths, Groups 1b, 2b, 5b, 6b, 7b, and 8 of the Periodic Table of the Elements, and mixtures thereof, and a, b, and c represent weight percent of the $Al_2O_3$, $SiO_2$, and $M_{2/n}O$ components, respectively, in the alumina-silica-metal oxide combination, with a being 0 to 100, b being 0 to 100, and c being 0 to 50, and n represents an integer from 1 to 7 of the valence of the metal cation, with the proviso that the sum of (a+b) must be greater than 0, and (b) a catalytically effective amount of sulfur trioxide.

Nitroaromatic compounds find use as solvents, explosives, dyes, perfumes, and analytical reagents, and are important as intermediates in organic synthesis. As an example, nitroaromatic compounds are convertible by reduction into primary amines, which, in turn, are valuable intermediates in the synthesis of dyes, pharmaceuticals, photographic developers, antioxidants, and gum inhibitors.

2. Description of the Prior Art

Nitroaromatic compounds are currently produced primarily via liquid phase reactions employing mixed acids. A sulfuric acid/nitric acid mixture is the most commonly employed industrial nitrating agent. Other mixed acids for nitration of aromatic compounds are acetic acid/nitric acid mixtures as described, for example, in U.S. Pat. No. 3,180,900. In U.S. Pat. No. 3,928,476, the latter type nitration is conducted over silica-alumina or alumina supports. A sulfonic acid/nitric acid mixture is disclosed as a nitrating agent for the nitration of halobenzenes in U.S. Pat. No. 3,077,502. Reportedly, the sulfonic acid causes a para directive effect, the effect of which is to increase the para-to-ortho isomer distribution above the usual ratio of 1.7.

Vapor phase nitration of aromatic compounds is also known in the art. The vapor phase nitration of benzene and toluene at temperatures ranging from about 275° C. to about 310° C. is described in McKee and Wilhelm, *Industrial and Engineering Chemistry*, 28(6), 662–667 (1936) and U.S. Pat. No. 2,109,873. McKee and Wilhelm catalyzed their reaction with silica gel, with best results being reported by the use of 14 mesh material. Bauxite and alumina were reported to be ineffective as catalysts in the vapor phase nitration of benzene. More recently, U.S. Pat. No. 4,107,220 described the vapor phase nitration of chlorobenzene in the presence of molecular sieve catalysts having a pore size varying from about 5 Å to about 10 Å as a means for controlling the para-to-ortho isomer distribution of nitrochlorobenzene. A suitable temperature range was reported to be from about 190° to about 290° C.

Although these prior art processes generally provide the desired product, the choice of available catalysts is severely limited. In addition, the commercial utility of a catalytic process is highly dependent upon the cost of the catalyst employed, the conversion of the reactant(s), and the yield of the desired product(s). In many cases, a reduction in the cost of the catalyst system employed in a given process on the order of a few cents per pound or a small percent increase in the yield of the desired product represents a tremendous commercial economical savings. Thus, the discovery that the vapor phase nitration reaction of the present invention can be carried out in a very efficient manner with high aromatic compound conversion and high nitroaromatic compound selectivity is believed to be a decided advance in the art.

SUMMARY OF THE INVENTION

It is an object of this invention to provide a vapor phase nitration process for converting aromatic compounds to the corresponding nitroaromatic compounds characterized by high aromatic compound conversion and high nitroaromatic compound selectivity. This and other objects, aspects, and advantages of the invention will become apparent to those skilled in the art from the accompanying description and claims.

The above objects are achieved by the improved process disclosed herein for the vapor phase nitration of aromatic compounds where the aromatic compound is contacted with a nitrating agent in the vapor phase to yield the corresponding nitroaromatic compound, the improvement comprising conducting the nitration in the presence of a nitration promoting catalyst which comprises the adduct of:

(a) an alumina-silica-metal oxide combination represented by the formula:

$$(Al_2O_3)_a(SiO_2)_b(M_{2/n}O)_c$$

wherein M is a metal cation selected from the group consisting of the lanthanides or rare earths, Groups 1b, 2b, 5b, 6b, 7b, and 8 of the Periodic Table of the Elements, and mixtures thereof, and a, b, and c represent weight percent of the $Al_2O_3$, $SiO_2$, and $M_{2/n}O$ components, respectively, in the alumina-silica-metal oxide combination, with a being 0 to 100, b being 0 to 100, and c being 0 to 50, and n is an integer from 1 to 7 of the valence of the metal cation, with the proviso that the sum of (a+b) must be greater than 0, and (b) a catalytically effective amount of sulfur trioxide.

DESCRIPTION OF THE PREFERRED EMBODIMENTS

In accordance with this invention, aromatic compounds are nitrated in the vapor phase via an improved process where the aromatic compound is contacted with a nitrating agent in the vapor phase to yield the corresponding nitroaromatic compound, the improvement comprising conducting the nitration in the presence of a nitration promoting catalyst which comprises the adduct of:

(a) an alumina-silica-metal oxide combination represented by the formula:

$(Al_2O_3)_a(SiO_2)_b(M_{2/n}O)_c$ wherein M is a metal cation selected from the group consisting of the lanthanides or rare earths, Groups 1b, 2b, 5b, 6b, 7b, and 8 of the Periodic Table of the Elements, and mixtures thereof, and a, b, and c represent weight percent of the $Al_2O_3$, $SiO_2$, and $M_{2/n}O$ components in the alumina-silica-metal oxide combination, with a being 0 to 100, b being 0 to 100, and c being 0 to 50, and n represents an integer from 1 to 7 of the valence of the metal cation, with the proviso that the sum of (a+b) must be greater than 0, and (b) a catalytically effective amount of sulfur trioxide. The process is characterized by high aromatic compound conversion and high nitroaromatic compound selectivity. And, in addition, when the aromatic compound starting material is a monosubstituted aromatic compound having an ortho-para orientation substituent, especially chlorobenzene, the observed para-to-ortho isomer distribution ranges from about 1.8–3.5/1, depending upon the particular nitration promoting catalyst and aromatic compound employed.

Aromatic compounds suitable for use in the present process are those which can exist in the vapor phase or state and undergo nitration under operating conditions to yield the desired nitroaromatic compounds. Moreover, in those instances where ortho and/or para isomers of the nitroaromatic compound are desired, the aromatic compound starting material must have an ortho-para orientation substituent such as halogen, lower alkyl, lower hydroxyalkyl, lower acetoxyalkyl, lower alkoxy, phenyl, and the like, where the term "lower alkyl" and related terms refer to substituents containing alkyl groups of 1 to 6 carbon atoms. Nonlimiting representatives of suitable aromatic compounds include aromatic hydrocarbons, such as benzene, toluene, xylenes, ethylbenzene, cumene, naphthalene, and the like; aromatic ethers such as anisole, phenetole, and the like; haloaromatic compounds such as chlorobenzene, bromobenzene, iodobenzene, o-dichlorobenzene, and the like; aromatic carboxylates such as benzoic acid, methyl benzoate, ethyl benzoate, and the like. It has been found, however, that the process of this invention is particularly efficacious with chlorobenzene (also known as monochlorobenzene or simply MCB), and benzene.

It will be apparent, of course, that mono-substituted aromatic compounds having an ortho-para orientation substituent—toluene and chlorobenzene, for example—upon being nitrated yield a nitroaromatic compound product containing ortho, meta, and para isomers. In such instances, the ortho and para isomers generally constitute the major portion of the product mixture, with the meta isomer being present in only trace amounts.

The nitrating agents which are employed in the process of this invention are the gaseous oxides of nitrogen higher than nitric oxide (NO) such as nitrogen dioxide ($NO_2$), dinitrogen trioxide ($N_2O_3$), and dinitrogen tetroxide ($N_2O_4$). Of these nitrating agents, nitrogen dioxide is preferred. Thus, for convenience and clarity, the process will be described with reference to the preferred nitrogen dioxide as the nitrating agent.

The nitration promoting catalyst employed in accordance with this invention is the adduct of:

(a) an alumina-silica-metal oxide combination represented by the formula:

$(Al_2O_3)_a(SiO_2)_b(M_{2/n}O)_c$ wherein M is a metal cation selected from the group consisting of the lanthanides or rare earths, Groups 1b, 2b, 5b, 6b, 7b, and 8 of the Periodic Table of the Elements, and mixtures thereof, and a, b, and c represent weight percent of the $Al_2O_3$, $SiO_2$, and $M_{2/n}O$ components, respectively, in the alumina-silica-metal oxide combination, with a being 0 to 100, b being 0 to 100, and c being 0 to 50, and n is an integer from 1 to 7 of the valence of the metal cation, with the proviso that the sum of (a+b) must be greater than 0, and (b) a catalytically effective amount of sulfur trioxide.

Alumina-silica-metal oxide combination materials suitable for use in the present invention are those which yield the nitration promoting catalyst compositions which are effective to catalyze the nitration of aromatic compounds in the vapor phase with high conversion of the reactants and high yield of desired products. Such materials may be crystalline, noncrystalline, or mixtures thereof. Nonlimiting representative examples of suitable alumina-silica-metal oxide combination materials are alumina (a=100; b=c=0), silica (b=100; a=c=0), alumina-silica, including aluminosilicates such as synthetic and naturally occurring zeolites, and mixtures thereof.

In many instances, it may be desirable to modify the physical and/or chemical properties of the alumina-silica-metal oxide combination or the distribution of products produced in the vapor phase nitration reaction of the present invention. To this end, one or more metal oxide components may be incorporated into the alumina-silica-metal oxide combination. Depending upon the particular effect desired or property to be modified, suitable metal oxides are those wherein the metal cation (M) is selected from the group consisting of the lanthanides or rare earths, Groups 1b, 2b, 5b, 6b, 7b, and 8 of the Periodic Table of the Elements, and mixtures thereof.

The alumina-silica-metal oxide combination materials are available commercially from numerous catalyst suppliers. Such materials can also be prepared by procedures well known in the art. For example, the alumina-silica-metal oxide combination materials wherein c is greater than 0 can be prepared by known procedures for preparing supported metal oxide catalysts. The method generally employed for producing such metal oxide catalysts involves impregnating the support—alumina, silica, and alumina-silica, for example—with a soluble metal salt convertible to the metal oxide, separating the saturated solid, and heating to remove a major portion of the solvent. The resultant material is then calcined to convert the metal salt to the corresponding metal oxide. In many cases, a multiple impregnation technique is employed to achieve a higher concentration to metal oxide on the support.

Another well-known technique involves suspending the support material in a solution of a metal salt convertible to the metal oxide, completely or partially evaporating the solvent, and possibly mixing of the resultant material with an organic binder and forming structures thereof. The dried structures are then heated to an elevated temperature to effect complete removal of solvent, burning out of the organic material, and as previously noted, conversion of the metal salt to the corresponding metal oxide.

The alumina-silica-metal oxide combination material need not necessarily be completely free of impurities.

Thus, materials or substances other than $Al_2O_3$, $SiO_2$, and $M_{2/n}O$ which cause little, if any, adverse effect upon the resultant catalyst's activity may be present. Impurities which are commonly associated with alumina and alumina-containing materials include, for example, oxides of the alkali metals, the alkaline earth metals, and titanium of Group 4b of the Periodic Table of the Elements. In general, such impurities may be present in amounts not exceeding 5 weight percent.

The term Periodic Table of the Elements, as employed herein refers to the Periodic Table of the Elements published in *CRC Handbook of Chemistry and Physics*, 60th, ed., Weast, Ed., CRC Press, Inc, Boca Raton, Fla., 1979, Inside Front Cover.

Sulfur trioxide ($SO_3$) is an essential component of the nitration promoting catalyst compositions employed in the vapor phase nitration process of the present invention. It is added to the alumina-silica-metal oxide combination in a catalytically effective amount. It may be charged directly as sulfur trioxide in the vapor or gaseous phase. Alternatively, it may be provided indirectly by charging to the alumina-silica-metal oxide combination a mixture of sulfur dioxide ($SO_2$) and nitrogen dioxide ($NO_2$) which react to produce sulfur trioxide and inert (for purposes of the present invention) nitric oxide (NO). When a mixture of sulfur dioxide and nitrogen dioxide is employed, a stoichiometric mole ratio of at least 1 is required. It is preferred, however, to employ an excess of sulfur dioxide, usually on the order of about 2 to 3 moles per mole of nitrogen dioxide.

In general, when providing the sulfur trioxide, the indirect method of charging a mixture of sulfur dioxide and nitrogen dioxide to the alumina-silica-metal oxide combination is preferred in that both sulfur dioxide and nitrogen dioxide, as well as nitric oxide, exist in the gaseous state at ambient temperatures (approximately 25° C.) and above while sulfur trioxide exists as a liquid at ambient temperatures and under the usual and preferred preparative conditions would first have to be converted to a vapor prior to contacting the alumina-silica-metal oxide combination.

As previously indicated, the nitration promoting catalyst compositions comprise an adduct, an essential component of which is sulfur trioxide. It is recognized, of course, that when a mixture of sulfur dioxide and nitrogen dioxide is charged to the reactor to provide the sulfur trioxide, the adsorbed species may in fact be a complex or combination of sulfur trioxide and nitrogen dioxide. However, regardless of the actual composition of the adsorbed species, it is conveniently referred to herein as sulfur trioxide and is meant to encompass all such compositions, whether sulfur trioxide, sulfur trioxide-nitrogen dioxide complex, or some combination thereof, as well as unreacted mixtures of sulfur dioxide and nitrogen dioxide.

The nitration promoting catalyst compositions useful to catalyze the process of the present invention are normally prepared by contacting the alumina-silica-metal oxide combination with sulfur trioxide (directly or indirectly as previously described) in the vapor phase under conditions conducive to the formation of the adduct and for a time sufficient to induce the desired weight gain. The amount of added sulfur trioxide (as indicated by the gain in weight) is not narrowly critical. All that is necessary is that a catalytically effective amount of sulfur trioxide be added. In general, it has been found that at least 5 weight percent, based on the weight of the alumina-silica-metal oxide combination, sulfur trioxide is required to provide the enhanced activity exhibited by the nitration promoting catalyst compositions. Also, although not critical, an upper limit of about 40 weight percent, with about 10 weight percent being preferred, has been found to be desirable in that little, if any, advantage is demonstrated for higher concentrations of sulfur trioxide. Thus, both higher and lower concentrations than the stated 5 to 40 weight percent range can be employed, if desired, but since such concentrations offer no particular advantage over the stated desirable range, and may in fact affect adversely the catalyst activity, particularly at concentrations less than about 5 weight percent, the stated 5 to 40 weight percent range is desirably employed.

The conditions under which the nitration promoting catalyst compositions are prepared can vary widely. All that is necessary is that the sulfur trioxide, whether charged directly or indirectly, exist in the vapor phase while contacting the alumina-silica-metal oxide combination. Thus, the catalyst preparation can be conducted at temperatures ranging from ambient temperatures (about 25° C.) (when sulfur dioxide and nitrogen dioxide are employed to provide the sulfur trioxide) to about 300° C. or higher. Preferred temperatures, however, range from about 150° C. to about 250° C., with 175° C. to about 225° C. being particularly preferred. At such preferred temperatures, the uptake of sulfur trioxide is reasonably rapid with a minimum of loss of reactant gases resulting from unreacted pass-through. In general, and for convenience, the catalyst preparations can be performed at the temperature to be employed in the subsequent vapor phase nitration reaction in which the catalyst is to be employed.

The nitration promoting catalyst preparations are conducted under substantially anhydrous conditions. This is necessary since sulfur trioxide readily undergoes reaction with water to form sulfuric acid which, prior to formation of the adducts comprising the catalyst compositions of the present invention, may exhibit an adverse effect in the subsequent vapor phase nitration reaction. As employed herein, the term "substantially anhydrous" means not more than 5 weight percent water is present in the reaction as part of the nitration promoting catalyst-forming components.

The nitration promoting catalyst compositions useful in the vapor phase nitration process of the present invention are conveniently prepared in an apparatus of the type suitable for carrying out chemical reaction in the vapor phase. In this manner the catalyst preparation can be performed in the same reactor as that to be employed for the subsequent vapor phase nitration reaction. It can be conducted in a fixed bed, moving bed, or a fluidized bed system to effect contacting of the alumina-silica-metal oxide combination and the sulfur trioxide. And, as previously noted, catalyst preparation is preferably carried out by continually passing a vaporous mixture of sulfur dioxide and nitrogen dioxide in a 2–3/1 mole ratio over a bed of the alumina-silica-metal oxide combination under substantially anhydrous conditions at a temperature from about 25° C. to about 300° C., and usually, about 175° C. to about 225° C.

If desired, the nitration promoting catalyst is conditioned by pretreatment with nitrogen dioxide at vapor phase nitration conditions (discussed hereinbelow) to the saturation point (in the absence of aromatic compounds). Suitable pretreatment times can range from about 1 minute to about 1 hour or more. The actual pretreatment time, however, will depend upon the amount or quantity and pore structure of the nitration promoting catalyst, the flow rate of the nitrogen dioxide, the operating conditions, and the like. When employed, pretreatment for about 5 minutes to about 15 or 20 minutes is usually sufficient.

The conditioning pretreatment is not a prerequisite for effective vapor phase nitration. In many instances, however, it is desirable because it permits almost immediate production of the nitroaromatic compound upon introduction of the aromatic compound to the reactor. In such instances, in the absence of the pretreatment, measurable nitroaromatic compound production may be delayed until the nitration promoting catalyst becomes saturated with nitrogen dioxide.

The vapor phase nitration process of this invention is not limited to a specific reaction temperature since the process can be conducted at temperatures ranging from about 80° C. to about 300° C. Preferred temperatures, however, range from about 150° C. to about 250° C., with 175° C. to about 225° C. being particularly preferred. At such preferred temperatures, the rate of reaction is reasonably rapid and little, if any, by-product formation occurs. It will be appreciated, however, that the particular temperature employed for a given aromatic compound will depend to some extent upon the boiling point or vaporization temperature of the particular aromatic compound. For example, when chlorobenzene, which has a boiling point of 132° C., is the aromatic compound of choice, the vapor phase nitration is conveniently carried out within the aforesaid preferred and most preferred temperature ranges. When benzene (b.p., 80° C.) is the aromatic compound of choice, the vapor phase nitration may be conducted at temperatures which encompass the entire operative temperature range, that is, from about 80° C. to about 300° C. Again, however, temperatures from about 150° C. to about 250° C. are preferred.

In a similar manner, when a solid compound such as naphthalene or benzoic acid (sublimation temperatures at atmospheric pressure, 80.2° C. and 100° C., respectively) is the aromatic compound of choice, the vapor phase nitration may be conducted at temperatures at or above the vaporization (sublimation) temperature, and preferably within the aforesaid preferred temperature range.

Notwithstanding the stated preferred temperature range, it will be appreciated that higher temperatures may be advantageously employed for more difficult to nitrate aromatic compounds. For example, o-dichlorobenzene (b.p., 179° C.) does not readily undergo nitration within the preferred temperature range of about 150° C. to about 250° C. Thus, in order to effect reasonable conversions and yields, temperatures greater than 250° C. to about 300° C. are preferred.

As previously indicated, the vapor phase nitration of this invention can be conducted at temperatures ranging from about 80° C. to about 300° C., with temperatures from about 150° C. to about 250° C. being preferred. Some advantages accruing from conducting the vapor phase nitration of this invention at the preferred temperatures include:

(a) greater selectivity to the desired nitroaromatic compounds;

(b) little, if any, by-product formation (to contaminate the desired product);

(c) high material balance between reactants and products; and (d) minimal thermal decomposition of the nitrogen dioxide.

The latter advantage [(d)] is particularly significant in that it, to a large extent, influences the remaining advantages. It, of course, is well-known in the art that at elevated temperatures nitrogen dioxide undergoes thermal decomposition into the inert (for purposes of this invention) nitric oxide and molecular oxygen. The decomposition begins at about 150° C. and is complete at about 620° C. The decomposition at various temperatures is as follows:

| Temperature, °C. | 130 | 150 | 184 | 279 | 494 | 620 |
|---|---|---|---|---|---|---|
| Decomposition, % | 0 | 3 | 5 | 13 | 56.5 | 100 |

Thus, at temperatures between about 80° C. and about 300° C., the maximum loss of active nitrogen dioxide by thermal decomposition into inert nitric oxide is only about 15–20%, while at temperatures greater than 300° C., the loss by thermal decomposition rapidly increases to 30% or more, and, finally, to 100% at 620° C. Clearly, the magnitude of the loss of nitrogen dioxide at temperatures higher than the usual operating temperatures of this invention and, in particular, the preferred temperature ranges, is wasteful and impractical. Moreover, if recirculation of the effluent stream from such high temperature processes is desired, in order to prevent the complete loss of inert nitric oxide, it is necessary to employ an additional step to reoxidize the nitric oxide to the active nitrogen dioxide by treatment thereof with oxygen or an oxygen-containing gas such as air, with the attendant added cost and complexity. The additional cost and complexity of this added step, however, is substantially reduced or eliminated altogether by the usual operating temperature conditions employed in the process of this invention.

Pressure is not critical in the process of this invention. The vapor phase nitration reaction may be carried out at subatmospheric, atmospheric, or superatmospheric pressures as desired. It will be appreciated that pressures in excess of atmospheric pressure may be advantageously employed as an aid in minimizing the previously discussed thermal decomposition of nitrogen dioxide, while subatmospheric pressures may be employed as an aid in vaporizing more difficult to vaporize aromatic compounds. It will be generally preferred, however, to conduct the reaction at or near atmospheric pressure. Generally, pressures from about $2.53 \times 10^4$ pascals or Pa (0.25 atmosphere or atm) to about $4.053 \times 10^5$ Pa (4.0 atm) may be conveniently employed.

The vapor phase nitration process of this invention is carried out in the presence of water, which is believed necessary to create and renew reaction sites on the nitration promoting catalyst. The required water can be supplied by water of hydration in the catalyst or, alternatively, by the separate addition of water via the feed stream. When water of hydration (within the previously defined substantially anhydrous limitation) is present, no added water is required since once the reaction is initiated, water produced during the course of the reaction (1 mole of water for each 2 moles of nitroaromatic compound produced) is sufficient to sustain it. If the nitration promoting catalyst is substantially free of water of hydration, it then becomes necessary to add water in an amount sufficient to provide the required reaction sites. Separate addition of water is usually preferred to ensure its presence in sufficient amount. The amount of water present, however, is not narrowly critical. Thus, amounts ranging from nominal or trace amounts (about 0.1 volume percent) up to about 15 percent by volume of the feed stream are generally sufficient, with amounts ranging from about 0.5 percent to about 5 percent by volume being desirably used.

The vapor phase nitration of this invention is conveniently carried out in an apparatus of the type suitable for carrying out chemical reactions in the vapor phase. It can be conducted in a single reactor or in multiple reactors using either a fixed bed, moving bed or a fluidized bed system to effect contacting of the reactants and the nitration promoting catalyst. Reaction is generally carried out by continuously passing a vaporous mixture of the aromatic compound and nitrogen dioxide over a bed of the nitration promoting catalyst while maintaining a temperature from about 80° C. to about 300° C., and, usually, about 175° C. to about 225° C.

The reactant aromatic compound can be preheated to form a vapor which is then admixed with gaseous nitrogen dioxide in a suitable reactor in predetermined relative proportions. The vaporous aromatic compound can be pumped into the reactor at a constant rate and admixed with a water-containing or humidified stream of gas and nitrogen dioxide before contacting the heated catalyst bed, or, alternatively, it can be conveniently swept into the reactor at a constant rate by a water-containing stream of carrier gas and thence admixed with a continuous stream of nitrogen dioxide before contacting the heated catalyst bed. The reactants can be charged into the reactor at any suitable flow rate.

As previously indicated, the reactant materials can be conveniently swept into the reactor by a stream of carrier gas. The carrier gas employed in the present process can be oxygen or an oxygen-containing gas, for example, air, or an inert gas such as nitrogen, helium, and the like. When employed, it is advantageous to employ oxygen or an oxygen-containing gas as the carrier gas (for the aromatic compound) due to the stoichiometry of the nitration reaction between the aromatic compound and the nitrogen dioxide. In addition, carrier gases preferred for the required water and nitrogen dioxide, respectively, are air and nitrogen.

In the initial nitration reaction between the aromatic compound and the nitrogen dioxide, it is believed that for each 2 moles of aromatic compound, 3 moles of nitrogen dioxide are required to produce 2 moles of nitroaromatic compound, 1 mole of nitric oxide, and 1 mole of water. In the absence of an oxygen source such as supplied by the oxygen-containing carrier gas, the nitric oxide is lost, thereby reducing the nitrogen dioxide selectivity to the nitroaromatic compound by at least 33% ($\frac{1}{3}$), as well as the material balance between reactants and recovered products. In the presence of oxygen (and the nitration promoting catalyst), however, the nitric oxide undergoes the known reoxidation to nitrogen dioxide (stoichiometrically requiring 1 mole of oxygen for each 2 moles of nitric oxide), which undergoes further reaction with additional aromatic compound. This known reoxidation of nitric oxide to nitrogen dioxide also serves to reduce the loss of nitrogen dioxide as nitric oxide via the previously discussed nitrogen dioxide thermal decomposition. Overall, therefore, little, if any, nitrogen dioxide is lost by virtue of stoichiometrically produced, as well as thermally produced, nitric oxide.

The concentration of the aromatic compound in the feed mixture is not narrowly critical. All that is necessary is that the concentration be sufficient to permit the reaction to proceed at a reasonable rate. On the other hand, since the nitroaromatic compound produced will have a high vaporization temperature (for example, nitrochlorobenzene isomers, b.p., 235°–246° C.), the concentration should be such that the nitroaromatic compound produced will not condense in the reactor. In addition, since mixtures of aromatic compounds and air (the preferred aromatic compound carrier gas) are potentially flammable and explosive, it is preferred, from a practical viewpoint, to operate at concentrations outside the flammable and explosive limits of the aromatic compound being employed. Generally, concentrations between about 1% and about 15% by volume are desirably employed.

The relative proportions of reactants generally can range from about 0.5 to 5 moles of nitrogen dioxide per mole of aromatic compound and, preferably, a ratio of about 1.5 to 4:1 is used.

The present process is suited to either batch or continuous operation. Continuous operations can involve recirculation of the effluent stream unreacted aromatic compound and nitrogen dioxide following isolation of the nitroaromatic compound product. Additional reactants—aromatic compounds and nitrogen dioxide—can then be charged to the reactor along with the recirculated stream to continue the process in a subsequent and continuous reaction. It will be noted that the substantial absence of side reactions, such as, for example, the thermal decomposition of nitrogen dioxide and undesired by-product formation advantageously facilitate such continuous operations in that extensive purification of the effluent stream is not required and, as previously noted, the cost and complexity of reoxidation of the nitric oxide to nitrogen dioxide is substantially reduced or eliminated altogether.

The nitroaromatic compounds produced during the course of the vapor phase reaction can be collected in a suitable chilled container, and purified by any appropriate method and means known to the art such as, for example, distillation and crystallization. Fractional crystallization in accordance with conventional procedures are especially convenient for the separation of ortho and para isomers when a monosubstituted aromatic compound having an ortho-para orientation substituent, such as chlorobenzene, is employed as the reactant or starting material.

The recovered unreacted reactants, due to the substantial absence of side-reactions to produce undesirable by-products, are easily recycled to the reactor for further processing.

The following specific examples illustrating the best presently-known methods of practicing this invention are described in detail in order to facilitate a clear understanding of the invention. It should be understood, however, that the detailed expositions of the application of the invention while indicating preferred embodiments, are given by way of illustration only and are not to be construed as limiting the invention since various changes and modifications within the spirit of the invention will become apparent to those skilled in the art from this detailed description.

EXAMPLES 1–15

Preparation of Catalysts

A stainless steel tube 40.64 (16 inches) in length and 2.54 cm (1 inch) outside diameter, was employed as the reactor. An alumina-silica-metal oxide combination material was placed in the reactor and dried, if necessary, by heating to about 225° C. under a constant stream of dry nitrogen for about 1 hour. The temperature was set at the preparation temperature, usually about 175° C., and sulfur dioxide, along with nitrogen dioxide (in a nitrogen carrier stream), unless specified otherwise, was charged to the reactor containing the alumina-silica-metal oxide combination in approximately a 2–3/1 mole ratio until the sulfur trioxide uptake had reached the desired amount. The time period was usually about 1 hour. The parameters and the results are tabulated in Table 1.

TABLE 1

ALUMINA-SILICA-METAL OXIDE COMBINATION[1]

| (EXAMPLE) CATALYST | Name[2] | $(Al_2O_3)_a$ a Wt % | $(SiO_2)_b$ b Wt % | $(M_{2/n}O)_c$ c Wt % |
|---|---|---|---|---|
| 1 | Boehmite[8] | 100 | 0 | 0 |
| 1a[9] | " | " | " | " |
| 2 | Zeolon 900H[8] | 9.4 | 90.6 | " |
| 2a[10] | " | " | " | " |
| 2b[11] | " | " | " | " |
| 3 | Silica-alumina[12] | 12 | 87 | " |
| 3a[13] | " | " | " | " |
| 3b[14] | " | " | " | " |
| 4 | " | " | " | " |
| 5[15] | Silica-alumina[16] | 50 | 50 | " |
| 5a[17] | " | " | " | " |
| 6 | Silica[18] | 0 | 100 | " |
| 7 | Silica gel[19] | " | " | " |
| 8[20] | Cobalt oxide-molybdenum oxide on alumina[16] | 86.5 | 0 | 13.5[21] |
| 8a[22] | Cobalt oxide-molybdenum oxide on alumina[16] | " | " | " |
| 9[23] | Cobalt oxide-molybdenum oxide on alumina[16] | 80.5 | " | 19.5[24] |
| 10[25] | Silica-alumina[26] | 45 | 53 | 0 |
| 10a[27] | " | " | " | " |
| 10b[28] | " | " | " | " |
| 10c[29] | " | " | " | " |
| 11[30] | Nickel oxide-tungsten oxide on silica-alumina[12] | 17.4 | 65 | 17.6[31] |
| 12[32] | Cobalt oxide on silica (α-quartz)[16] | 0 | 83.7 | 16.3[33] |
| 13[34] | Alumina[8] | 100 | 0 | 0 |
| 14 | Silica-alumina[12] | 12 | 87 | 0 |
| 15 | " | " | " | " |

ALUMINA-SILICA-METAL OXIDE COMBINATION[1] — Physical Properties

| (EXAMPLE) CATALYST | Surface Area m²/g | Size, cm. | Shape | Amount, g Initial[3] | Amount, g Final[4] |
|---|---|---|---|---|---|
| 1 | 292.2 | 0.32 × 0.32 | Pellets | 112.9 | 103.6 |
| 1a[9] | " | " | " | " | " |
| 2 | 400–450 | " | " | 98.9 | 86.1 |
| 2a[10] | " | " | " | " | " |
| 2b[11] | " | " | " | " | " |
| 3 | 425–450 | " | " | 84.7 | 83.1 |
| 3a[13] | " | " | " | " | " |
| 3b[14] | " | " | " | " | " |
| 4 | " | " | " | 83.6 | 80.4 |
| 5[15] | 260 | 0.64 × 0.64 | Tablets | — | 105.5 |
| 5a[17] | " | " | " | " | " |
| 6 | 350 | 0.14–0.48 | Spheres | — | 54.8 |
| 7 | — | 0.12–0.34 | Crystallite | 92.4 | 90.4 |
| 8[20] | " | 0.32 × 0.32 | Pellets | — | 100.4 |
| 8a[22] | " | " | " | " | " |
| 9[23] | " | 0.34–0.48 | Spheres | " | 125.2 |
| 10[25] | " | 0.38 × 0.38 | Pellets | " | 120.1 |
| 10a[27] | " | " | " | " | " |
| 10b[28] | " | " | " | " | " |
| 10c[29] | " | " | " | " | " |
| 11[30] | 230 | 0.21 × 0.21 | " | " | 101.0 |
| 12[32] | 110 | 0.40–0.64 | Spheres | " | " |
| 13[34] | 306 | 0.32 | " | " | 92.8 |
| 14 | 425–450 | 0.32 × 0.32 | Pellets | " | 87.0 |
| 15 | " | " | " | " | 91.3 |

CATALYST PREPARATION CONDITIONS

| (EXAMPLE) CATALYST | SULFUR TRIOXIDE UPTAKE g, wt. %[5] (Totals)[6] | Flow Rate ml/min. Sulfur Dioxide | Flow Rate ml/min. Nitrogen Dioxide | Flow Rate ml/min. Carrier Gas[7] | Time Hours | Temp. °C. |
|---|---|---|---|---|---|---|
| 1 | 12.5, 12.1 | 107.0 | 49.0 | 31.0 | 1.0 | 175 |
| 1a[9] | 8.9, 8.6 | 129.0 | 154.0 | " | " | " |
|  | (21.4, 20.6) | | | | | |
| 2 | 9.1, 10.6 | 107.6 | 53.6 | " | " | " |
| 2a[10] | 5.2, 6.0 | 108.0 | 54.0 | " | " | " |
|  | (14.3, 16.6) | | | | | |
| 2b[11] | 1.1, 1.3 | " | " | " | " | " |
|  | (15.4, 17.9) | | | | | |
| 3 | 7.9, 9.5 | 107.0 | " | " | " | " |
| 3a | 11.8, 14.2 | " | 60.0 | " | " | " |
|  | (19.7, 23.7) | | | | | |
| 3b | 10.1, 12.2 | " | " | 26.3 | " | " |
|  | (29.8, 35.9) | | | | | |
| 4 | 32.2, 40.0 | " | 62.9 | 30.0 | 3.0 | 180 |
| 5[15] | 10.6, 10.0 | " | 48.8 | 31.0 | 1.0 | 175 |
| 5a[17] | 11.6, 11.0 | " | " | " | " | " |
|  | (22.2, 21.0) | | | | | |
| 6 | 11.5, 21.0 | " | " | " | 1.5 | " |
| 7 | 12.3, 13.6 | " | 60.0 | " | 1.0 | " |
| 8[20] | 5.8, 5.8 | 141.0 | 62.0 | " | 0.5 | " |
| 8a[22] | 4.7, 4.7 | 131.0 | 56.0 | " | 0.5 | " |
|  | (10.5, 10.5) | | | | | |
| 9[23] | 8.4, 6.7 | " | 46.0 | " | 1.0 | " |
| 10[25] | 6.1, 5.1 | 142.0 | 67.4 | " | 0.5 | " |
| 10a[27] | 2.7, 2.2 | 58.0 | 30.0 | " | " | " |
|  | (8.8, 7.3) | | | | | |
| 10b[28] | 2.9, 2.4 | 78.0 | 36.0 | " | " | " |
|  | (11.7, 9.7) | | | | | |
| 10c[29] | 4.8, 4.0 | 124.0 | 59.0 | " | " | " |
|  | (16.5, 13.7) | | | | | |
| 11[30] | 5.2, 5.1 | 128.0 | 41.0 | " | 1.0 | " |
| 12[32] | 12.5, 14.6 | 150.0 | 60.0 | " | " | " |
| 13[34] | 11.2, 12.1 | 53.5 | 54.0 | 21.3 | 2.0 | " |
| 14 | 19.6, 22.5 | 126.0 | 55.0 | 31.0 | 2.5 | " |

TABLE 1-continued

| | | | | | | |
|---|---|---|---|---|---|---|
| 15 | 20.5, 22.5 | " | " | " | 2.2 | " |

[1]Composition and properties provided by commerical supplier unless otherwise noted.
[2]Material added initially to reactor.
[3]Weight in grams prior to drying, if subsequently dried.
[4]Weight in grams after drying, if dried.
[5]Based on the weight of the alumina-silica-metal oxide combination material.
[6]The total amount of sulfur trioxide taken up by the alumina-silica-metal oxide combination material as a result of a second, third, and the like addition, as applicable, of a sulfur trioxide source, usually sulfur dioxide and nitrogen dioxide, to a previously prepared adduct.
[7]Nitrogen; carrier gas for nitrogen dioxide.
[8]Available commercially from Norton Company, Akron, Ohio 44309.
[9]Catalyst 1, after use, was purged with steam at 225° C. for 1 hour, followed by dry nitrogen at 225° C. for an additional hour, and then contacted with additional sulfur dioxide and nitrogen dioxide to provide a total sulfur trioxide uptake.
[10]Catalyst 2, after two vapor phase nitration runs, was treated as described in Footnote 9.
[11]Catalyst 2a, after one vapor phase nitration run, was treated as described in Footnote 9.
[12]Available commerically from Strem Chemicals, Inc., Newburyport, Massachusetts 01950; contained 1.0% unidentified material.
[13]Catalyst 3, after two vapor phase nitration runs, was treated with additional sulfur dioxide and nitrogen dioxide for 1 hour.
[14]Catalyst 3a, after one vapor phase nitration run, was treated as described in Footnote 13.
[15]After one vapor phase nitration run, on virgin silica-alumina (catalyst precursor) for comparative purposes (Example 34), the catalyst composition of this invention was prepared.
[16]Available commerically from United Catalysts, Inc., Louisville, Kentucky 40232.
[17]Catalyst 5, after one vapor phase nitration run, was treated as described in Footnote 13.
[18]Available commerically from Air Products and Chemicals, Inc., Allentown, Pennsylvania 18105.
[19]Available commerically from Fisher Scientific Company, Fairhaven, New Jersey 07410.
[20]After one vapor phase nitration run on virgin alumina-silica-metal oxide combination material (catalyst precursor) for comparative purposes (Example 46), the catalyst composition of this invention was prepared.
[21]M represents a mixture of cobalt (n = 2; 3.5%) and molybdenum (n = 6; 10.0%) such that c is 13.5%.
[22]Catalyst 8, after one vapor phase nitration run, was treated with sulfur dioxide and nitrogen dioxide for an additional 30 minutes.
[23]After one vapor phase nitration run on virgin alumina-silica-metal oxide combination material (catalyst precursor) for comparative purposes (Example 49), the catalyst composition of this invention was prepared by treating the alumina-silica-metal oxide combination with sulfur dioxide and nitrogen dioxide for 1 hour.
[24]M represents a mixture of cobalt (n = 2; 4.5%) and molybdenum (7 = 6; 15.0%) such that c is 19.5%.
[25]After one vapor phase nitration run on virgin alumina-silica-metal oxide combination material (catalyst precursor) for comparative purposes (Example 51), the catalyst composition of this invention was prepared.
[26]Available commercially from Ventron Corporation, Alfa Products, Danvers, Massachusetts 01923; contained 2.0% unidentified materials.
[27]Catalyst 10, after one vapor phase nitration run, was treated with additional sulfur dioxide and nitrogen dioxide.
[28]Catalyst 10a, after one vapor phase nitration run, was treated with additional sulfur dioxide and nitrogen dioxide.
[29]Catalyst 10b, after one vapor phase nitration run, was treated with additional sulfur dioxide and nitrogen dioxide.
[30]After one vapor phase nitration run on virgin alumina-silica-metal oxide combination material (catalyst precursor) for comparative purposes (Example 56), the catalyst composition was prepared.
[31]M represents a mixture of nickel (n = 2; 3.3%) and tungsten (n = 6; 14.3%) such that c is 17.6%. Composition determined by semiquantitative x-ray fluorescence.
[32]After one vapor phase nitration run on virgin alumina-silica-metal oxide combination material (catalyst precursor) for comparative purposes (Example 58), the catalyst composition was prepared.
[33]M represents cobalt (n = 2 and 3; 16.3%).

EXAMPLES 16–74

Nitration Reaction

Using the reactor system described in Examples 1-5 for preparation of the catalysts, a number of reactions were run to show the effectiveness of the nitration promotion catalyst compositions as catalysts in the vapor phase nitration of aromatic compounds.

A stream of aromatic compound was preheated and charged to the reactor tube in a humidified or water-containing stream of air. The nitrating agent, nitrogen dioxide unless otherwise specified, in a nitrogen carrier stream was mixed with the aromatic compound/air stream shortly before contact with the heated catalyst. The products were collected in a series of three chilled containers, the first of which was chilled in an ice water bath and the second and third of which were chilled in dry ice baths. Analyses were performed by gas chromatography on a Varian Associates Model 3700 instrument using a 1.83-meter (6-ft.) by 0.32-cm (0.125-inch) outside diameter column, packed with 0.5 percent phosphoric acid on 5/95 weight percent SP-1000/Chromosorb G [carboxylic acid terminated poly(ethylene nitroterephthalate) from poly(ethylene glycol), M.W., 20,000, and nitroterephthalic acid, Supelco, Inc., Bellefonte, Pa. 16823/diatomaceous earth, Johns-Manville Products Corp., Manville, N.J. 08835] and programmed from 90° C. to 210° C. at a program rate of 10° C./min. The parameters and results are tabulated in Table 2.

TABLE 2

| Example | (Catalyst Number) | Aromatic Compound, R—C₆H₅ R | Flow Rate ml/min. | g, moles |
|---|---|---|---|---|
| 16 | 1 | Cl | 22.38 | 27.0, 0.24 |
| 17 | 1a | " | 24.83 | 29.9, 0.27 |
| 18 | 2 | " | 27.40 | 41.3, 0.37 |
| 19 | 2a | " | 30.27 | 31.9, 0.28 |
| 20 | 2b | " | 12.03 | 14.8, 0.13 |
| 21 | 3 | " | 21.80 | 23.5, 0.21 |
| 22 | 3 | " | 25.83 | 46.7, 0.42 |
| 23 | 3a | " | 30.02 | 45.2, 0.40 |
| 24 | 3b | " | 17.86 | 32.3, 0.29 |
| 25 | 4 | " | 21.88 | 36.3, 0.32 |
| 26 | 4 | " | 21.89 | 39.6, 0.35 |
| 27 | 4[6] | " | 20.79 | 31.3, 0.28 |
| 28 | 4[7] | " | 69.96 | 116.0, 1.03 |
| 29 | 4[7] | " | 40.02 | 72.4, 0.64 |
| 30 | 4[7] | " | 25.27 | 45.7, 0.41 |
| 31 | 4[8] | " | 23.71 | 35.7, 0.32 |
| 32 | 4[9] | H | 93.26 | 48.7, 0.62 |
| 33 | 4[10] | H | 87.97 | 36.8, 0.47 |
| 34 | 5-P[5] | Cl | 31.47 | 66.8, 0.59 |
| 35 | 5 | " | 31.73 | 56.9, 0.51 |
| 36 | 5a | " | 28.00 | 51.1, 0.45 |
| 37 | 5a | " | 14.93 | 31.6, 0.28 |
| 38 | 6 | " | 31.24 | 47.1, 0.42 |
| 39 | 6 | " | 29.05 | 43.8, 0.39 |
| 40 | 6 | " | 17.42 | 31.0, 0.28 |
| 41 | 7 | " | 21.92 | 33.0, 0.29 |
| 42 | 7 | " | 30.23 | 54.7, 0.49 |
| 43 | 7 | " | 24.87 | 52.5, 0.47 |
| 44 | 7 | " | 19.22 | 34.8, 0.31 |
| 45 | 7 | " | 23.80 | 43.0, 0.38 |
| 46 | 8-P[5] | " | 25.79 | 42.1, 0.38 |
| 47 | 8 | " | 24.64 | 36.9, 0.33 |
| 48 | 8a | " | 24.12 | 47.6, 0.42 |
| 49 | 9-P[5] | " | 21.89 | 38.5, 0.34 |
| 50 | 9 | " | 13.44 | 20.2, 0.18 |
| 51 | 10-P[5] | " | 23.15 | 34.7, 0.31 |
| 52 | 10 | " | 22.23 | 31.4, 0.28 |
| 53 | 10a | " | 23.02 | 41.6, 0.37 |
| 54 | 10b | " | 23.02 | 41.5, 0.37 |
| 55 | 10c | " | 21.72 | 35.8, 0.32 |
| 56 | 11-P[5] | " | 23.02 | 41.2, 0.37 |
| 57 | 11 | " | 12.69 | 18.6, 0.17 |
| 58 | 12-P[5] | " | 21.04 | 35.3, 0.31 |
| 59 | 12 | " | 23.15 | 35.1, 0.31 |
| 60 | 13-P[5] | " | 22.44 | 23.1, 0.21 |
| 61 | 13 | " | 19.98 | 27.1, 0.24 |
| 62 | 14[11] | H | 54.06 | 56.5, 0.72 |
| 63[12] | " | " | 54.60 | 57.0, 0.73 |
| 64 | " | " | 42.71 | 44.6, 0.57 |
| 65[12] | " | " | 40.92 | 42.8, 0.55 |
| 66 | " | " | 41.88 | 43.8, 0.56 |
| 67 | " | " | 40.27 | 42.1, 0.54 |
| 68 | " | " | 40.99 | 47.1, 0.60 |
| 69 | " | CH₃ | 30.99 | 35.2, 0.38 |
| 70 | " | " | 29.09 | 41.3, 0.45 |
| 71 | " | " | 33.45 | 41.2, 0.45 |
| 72 | " | " | 36.50 | 40.1, 0.44 |
| 73 | 15[13] | C₂H₅O | 38.35 | 58.6, 0.55 |

TABLE 2-continued

| Example | | | | |
|---|---|---|---|---|
| 74 | " | " | 27.38 | 44.8, 0.42 |

Aromatic Compounds, R—C$_6$H$_5$

| Example | Conc. vol. % | Temp. °C. | Carrier Gas[3] Flow Rate ml/min. |
|---|---|---|---|
| 16 | 3.1 | 80 | 500.0 |
| 17 | 3.4 | " | " |
| 18 | 3.7 | " | " |
| 19 | 4.2 | " | " |
| 20 | 1.8 | " | " |
| 21 | 3.0 | " | " |
| 22 | 3.5 | " | " |
| 23 | 4.1 | " | " |
| 24 | 2.5 | " | " |
| 25 | 3.1 | 85 | " |
| 26 | 3.2 | " | " |
| 27 | 3.0 | " | " |
| 28 | 6.4 | " | 850.0 |
| 29 | 5.0 | " | 600.0 |
| 30 | 3.6 | " | 500.0 |
| 31 | 3.3 | " | " |
| 32 | 10.7 | 30 | " |
| 33 | 9.8 | " | " |
| 34 | 4.3 | 85 | 500.0 |
| 35 | 4.4 | " | " |
| 36 | 3.8 | " | " |
| 37 | 2.1 | " | " |
| 38 | 4.3 | " | " |
| 39 | 4.0 | " | " |
| 40 | 2.5 | " | " |
| 41 | 3.0 | 80 | " |
| 42 | 4.1 | " | " |
| 43 | 3.5 | " | " |
| 44 | 2.8 | " | " |
| 45 | 3.5 | " | " |
| 46 | 3.3 | 82 | " |
| 47 | 3.2 | " | " |
| 48 | 3.2 | " | " |
| 49 | 2.9 | " | " |
| 50 | 2.7 | " | 320.0 |
| 51 | 3.2 | 85 | 500.0 |
| 52 | 2.9 | 82 | " |
| 53 | 3.0 | " | " |
| 54 | 3.0 | " | " |
| 55 | 2.9 | " | " |
| 56 | 3.0 | " | " |
| 57 | 2.5 | " | 320.0 |
| 58 | 2.7 | " | 500.0 |
| 59 | 3.0 | " | " |
| 60 | 3.1 | 80 | " |
| 61 | 2.8 | " | " |
| 62 | 9.4 | 21 | — |
| 63[12] | 8.6 | " | — |
| 64 | 7.5 | 21 | — |
| 65[12] | 6.9 | " | — |
| 66 | 7.3 | 23 | — |
| 67 | 7.3 | 22 | — |
| 68 | 7.2 | 18 | — |
| 69 | 5.9 | 21 | — |
| 70 | 5.6 | " | — |
| 71 | 4.7 | " | — |
| 72 | 5.0 | " | — |
| 73 | 6.7 | " | — |
| 74 | 2.5 | " | — |

Nitrating Agent[1]

| Example | Flow Rate ml/min. | g, moles | Conc. vol. % | Temp. °C. | Carrier Gas[4] Flow Rate ml/min. |
|---|---|---|---|---|---|
| 16 | 54.66 | 26.9, 0.58 | 7.7 | 15 | 31.0 |
| 17 | 66.23 | 32.6, 0.71 | 9.1 | " | " |
| 18 | 56.34 | 34.7, 0.75 | 7.8 | " | " |
| 19 | 61.66 | 26.6, 0.59 | 8.5 | " | " |
| 20 | 41.44 | 20.8, 0.45 | 6.0 | " | " |
| 21 | 54.29 | 24.0, 0.52 | 7.6 | " | " |
| 22 | 65.02 | 48.1, 1.05 | 8.8 | " | " |
| 23 | 60.18 | 37.1, 0.81 | 8.2 | " | " |
| 24 | 45.11 | 33.4, 0.73 | 6.4 | " | " |
| 25 | 62.92 | 42.6, 0.93 | 8.8 | " | 30.0 |
| 26 | 38.82 | 28.7, 0.62 | 5.7 | " | 21.0 |
| 27 | 26.59 | 16.4, 0.36 | 3.9 | " | 19.0 |
| 28 | 39.91 | 27.0, 0.59 | 3.6 | " | " |
| 29 | 30.43 | 22.5, 0.49 | 3.8 | " | " |
| 30 | 33.78 | 25.0, 0.54 | 4.8 | " | " |
| 31 | 41.75 | 25.7, 0.56 | 5.8 | " | 21.0 |
| 32 | 98.69 | 30.4, 0.66 | 11.3 | " | 47.5 |
| 33 | 116.34 | 28.7, 0.62 | 13.0 | " | 69.0 |
| 34 | 49.07 | 42.1, 0.92 | 6.8 | " | 31.0 |
| 35 | 49.15 | 36.3, 0.79 | 6.8 | " | " |
| 36 | 53.51 | 39.4, 0.86 | 7.4 | " | " |
| 37 | 36.27 | 31.5, 0.68 | 5.1 | " | " |
| 38 | 55.68 | 34.3, 0.75 | 7.6 | " | " |
| 39 | 51.13 | 31.5, 0.68 | 7.1 | " | " |
| 40 | 35.47 | 26.0, 0.57 | 5.1 | " | " |
| 41 | 60.63 | 37.4, 0.81 | 8.3 | " | " |
| 42 | 55.62 | 41.1, 0.89 | 7.6 | " | " |
| 43 | 48.00 | 41.4, 0.90 | 6.7 | " | " |
| 44 | 37.60 | 27.8, 0.60 | 5.5 | " | 21.0 |
| 45 | 37.01 | 27.4, 0.60 | 5.4 | " | " |
| 46 | 55.66 | 37.8, 0.82 | 7.2 | 12 | 31.0 |
| 47 | 53.76 | 33.2, 0.72 | 7.0 | " | " |
| 48 | 51.12 | 40.8, 0.89 | 6.7 | " | " |
| 49 | 48.92 | 34.8, 0.76 | 6.5 | " | " |
| 50 | 29.12 | 17.9, 0.39 | 5.7 | " | 24.0 |
| 51 | 57.49 | 35.6, 0.77 | 8.0 | " | 31.0 |
| 52 | 59.73 | 33.0, 0.72 | 7.8 | " | " |
| 53 | 52.89 | 39.3, 0.85 | 7.1 | " | " |
| 54 | 51.02 | 37.9, 0.82 | 6.7 | " | " |
| 55 | 55.27 | 35.6, 0.77 | 6.9 | " | " |
| 56 | 47.91 | 35.4, 0.77 | 6.3 | " | " |
| 57 | 25.39 | 15.8, 0.34 | 5.0 | " | 24.0 |
| 58 | 60.41 | 40.8, 0.89 | 7.8 | " | 31.0 |
| 59 | 52.27 | 32.3, 0.70 | 6.8 | " | " |
| 60 | 72.12 | 30.4, 0.66 | 9.9 | 15 | 30.0 |
| 61 | 69.80 | 38.7, 0.84 | 9.6 | " | " |
| 62 | 67.52 | 41.6, 0.90 | 11.7 | 10 | 29.0 |
| 63[12] | 97.42 | 60.0, 1.30 | 15.4 | 15 | 50.0 |
| 64 | 67.18 | 41.4, 0.90 | 11.8 | 10 | 29.0 |
| 65[12] | 85.07 | 52.4, 1.14 | 14.3 | 15 | 45.0 |
| 66 | 73.71 | 45.4, 0.99 | 12.9 | 10 | 29.0 |
| 67 | 42.97 | 26.5, 0.58 | 7.8 | " | " |
| 68 | 69.35 | 47.0, 1.02 | 12.2 | " | " |
| 69 | 48.61 | 24.0, 0.52 | 9.2 | " | " |
| 70 | 37.22 | 22.9, 0.50 | 7.2 | " | " |
| 71 | 43.58 | 26.8, 0.58 | 6.1 | " | 36.5 |
| 72 | 62.12 | 38.3, 0.83 | 8.5 | 15 | " |
| 73 | 65.98 | 37.9, 0.82 | 11.6 | 10 | " |
| 74 | 68.29 | 42.1, 0.92 | 6.1 | " | " |

Water

| Example | Nitrating Agent/ Aromatic Compound molar ratio | Flow Rate ml/ min. | g, moles | Conc. vol. % | Temp. °C. | Carrier Gas[3] Flow Rate ml/ min |
|---|---|---|---|---|---|---|
| 16 | 2.42 | 7.67 | 1.5, 0.082 | 1.1 | 80 | 98.0 |
| 17 | 2.63 | 6.84 | 1.3, 0.072 | 0.9 | " | " |
| 18 | 2.03 | 10.62 | 2.6, 0.14 | 1.5 | " | " |
| 19 | 2.11 | 7.70 | 1.3, 0.072 | 1.0 | " | " |
| 20 | 3.46 | 4.77 | 0.9, 0.050 | 0.7 | " | " |
| 21 | 2.48 | 12.33 | 2.1, 0.12 | 1.7 | " | " |
| 22 | 2.50 | 20.12 | 5.8, 0.32 | 2.7 | " | " |
| 23 | 2.02 | 16.55 | 4.0, 0.55 | 2.2 | " | " |
| 24 | 2.52 | 15.94 | 4.6, 0.26 | 2.3 | " | " |
| 25 | 2.91 | 3.13 | 0.8, 0.044 | 0.4 | 85 | " |
| 26 | 1.77 | 0.14 | 0.04, 0.0022 | 0.02 | " | " |
| 27 | 1.29 | 24.31 | 5.9, 0.33 | 3.5 | " | " |
| 28 | 0.57 | 17.61 | 4.7, 0.26 | 1.6 | " | " |
| 29 | 0.77 | 18.29 | 5.3, 0.29 | 2.3 | " | " |
| 30 | 1.32 | 27.86 | 8.1, 0.45 | 4.0 | " | " |
| 31 | 1.75 | 34.80 | 8.4, 0.47 | 4.8 | " | " |
| 32 | 1.06 | 38.00 | 4.6, 0.26 | 4.3 | " | " |
| 33 | 1.32 | 23.02 | 2.2, 0.12 | 2.6 | " | " |
| 34 | 1.56 | 16.53 | 5.6, 0.31 | 2.3 | " | " |
| 35 | 1.55 | 16.80 | 4.8, 0.27 | 2.3 | " | " |
| 36 | 1.91 | 16.80 | 4.9, 0.27 | 2.3 | " | " |
| 37 | 2.43 | 28.26 | 9.5, 0.53 | 4.0 | " | " |
| 38 | 1.79 | 12.86 | 3.1, 0.17 | 1.8 | " | " |
| 39 | 1.74 | 15.76 | 3.8, 0.21 | 2.2 | " | " |
| 40 | 2.04 | 14.93 | 4.3, 0.24 | 2.1 | " | " |
| 41 | 2.79 | 21.16 | 5.1, 0.28 | 2.9 | 80 | " |
| 42 | 1.82 | 15.73 | 11.6, 0.64 | 2.2 | " | " |

TABLE 2-continued

| Ex | | | | | | | |
|---|---|---|---|---|---|---|---|
| 43 | 1.91 | 11.85 | 4.0, 0.22 | 1.7 | " | " | |
| 44 | 1.94 | 7.81 | 2.3, 0.13 | 1.1 | " | " | |
| 45 | 1.58 | 6.26 | 1.8, 0.10 | 0.9 | " | " | |
| 46 | 2.16 | 25.12 | 6.7, 0.37 | 3.3 | 88 | 135.0 | |
| 47 | 2.18 | 26.13 | 6.3, 0.35 | 3.4 | " | " | |
| 48 | 2.12 | 22.97 | 7.2, 0.40 | 3.0 | " | " | |
| 49 | 2.24 | 14.80 | 4.2, 0.23 | 2.0 | " | " | |
| 50 | 2.17 | 16.43 | 4.0, 0.22 | 3.2 | " | 105.0 | |
| 51 | 2.48 | 8.21 | 2.0, 0.11 | 1.1 | 85 | 98.0 | |
| 52 | 2.57 | 19.91 | 4.3, 0.24 | 2.6 | 88 | 135.0 | |
| 53 | 2.30 | 20.53 | 5.9, 0.33 | 2.7 | " | " | |
| 54 | 2.22 | 24.27 | 7.0, 0.39 | 3.2 | " | " | |
| 55 | 2.41 | 20.36 | 5.4, 0.30 | 2.7 | " | " | |
| 56 | 2.08 | 23.02 | 6.6, 0.37 | 3.0 | " | " | |
| 57 | 2.00 | 16.43 | 4.0, 0.22 | 3.3 | " | 105.0 | |
| 58 | 2.87 | 22.40 | 6.0, 0.33 | 2.9 | " | 135.0 | |
| 59 | 2.26 | 21.65 | 5.3, 0.29 | 2.8 | " | " | |
| 60 | 3.14 | 8.89 | 1.5, 0.083 | 1.2 | 80 | 98.0 | |
| 61 | 3.50 | 6.91 | 1.5, 0.083 | 1.0 | " | " | |
| 62 | 1.25 | 20.48 | 5.0, 0.28 | 3.6 | 40 | 405 | |
| 63[12] | 1.78 | 25.80 | 6.2, 0.34 | 4.1 | 50 | " | |
| 64 | 1.58 | 23.85 | 5.8, 0.32 | 4.2 | 40 | " | |
| 65[12] | 2.07 | 19.41 | 4.7, 0.29 | 3.3 | " | " | |
| 66 | 1.77 | 23.89 | 5.8, 0.32 | 4.2 | " | " | |
| 67 | 1.07 | 30.95 | 7.5, 0.42 | 5.6 | 50 | " | |
| 68 | 1.70 | 23.57 | 6.2, 0.34 | 4.2 | 50 | " | |
| 69 | 1.37 | 14.31 | 2.8, 0.16 | 2.7 | 41 | " | |
| 70 | 1.11 | 19.08 | 4.6, 0.26 | 3.7 | " | " | |
| 71 | 1.29 | 23.44 | 5.6, 0.31 | 3.3 | " | 580 | |
| 72 | 1.89 | 17.92 | 4.3, 0.24 | 2.4 | 40 | " | |
| 73 | 1.49 | 23.91 | 5.4, 0.30 | 4.2 | " | 405 | |
| 74 | 2.19 | 42.23 | 10.2, 0.57 | 3.8 | 34.5 | 940 | |

| | Reaction Conditions | | Con- ver- sion, %[2] | Products, % R—$C_6H_4$—$NO_2$ R = $CH_3$, $C_2H_5O$, Cl | | | |
|---|---|---|---|---|---|---|---|
| Example | Temp. °C. | Time Hours | | R = H | ortho | meta | para |
| 16 | 175 | 4.0 | 41.0 | — | 9.8 | 0.9 | 30.3 |
| 17 | " | " | 49.8 | — | 13.8 | 1.0 | 34.4 |
| 18 | " | 5.0 | 77.6 | — | 20.3 | 1.6 | 55.5 |
| 19 | " | 3.5 | 81.1 | — | 22.2 | 1.2 | 57.7 |
| 20 | " | 4.1 | 96.4 | — | 24.6 | 1.4 | 70.4 |
| 21 | " | 3.6 | 88.5 | — | 23.2 | 1.4 | 63.9 |
| 22 | " | 6.0 | 66.4 | — | 16.7 | 1.1 | 48.6 |
| 23 | " | 5.0 | 85.0 | — | 24.3 | 1.7 | 59.0 |
| 24 | " | 6.0 | 93.4 | — | 28.1 | 1.8 | 63.6 |
| 25 | 180 | 5.5 | 99.7 | — | 28.6 | 1.6 | 69.5 |
| 26 | " | 6.0 | 78.4 | — | 22.9 | 1.3 | 53.5 |
| 27 | " | 5.0 | 67.7 | — | 20.1 | 0.8 | 46.4 |
| 28 | " | 5.5 | 22.1 | — | 6.4 | 0.4 | 15.0 |
| 29 | " | 6.0 | 36.1 | — | 10.5 | 0.5 | 24.8 |
| 30 | " | " | 71.9 | — | 19.6 | 1.0 | 51.2 |
| 31 | " | 50 | 88.1 | — | 26.2 | 1.3 | 60.6 |
| 32 | 160 | 2.5 | 66.8 | 66.3 | — | — | — |
| 33 | " | 2.0 | 83.1 | 82.2 | — | — | — |
| 34 | 175 | 7.0 | 1.8 | — | 0.6 | — | 1.2 |
| 35 | " | 6.0 | 49.8 | — | 13.3 | — | 36.5 |
| 36 | " | 6.0 | 44.3 | — | 13.3 | — | 31.1 |
| 37 | " | 7.0 | 51.7 | — | 14.8 | 0.6 | 35.1 |
| 38 | " | 5.0 | 67.1 | — | 21.6 | 1.4 | 44.2 |
| 39 | " | " | 74.2 | — | 35.8 | 2.4 | 46.0 |
| 40 | " | 6.0 | 93.6 | — | 30.2 | 1.9 | 61.4 |
| 41 | — | 5.0 | 90.9 | — | 24.1 | 1.6 | 65.2 |
| 42 | " | 6.0 | 77.7 | — | 24.0 | 1.2 | 52.5 |
| 43 | 180 | 7.0 | 86.9 | — | 25.8 | 1.4 | 59.6 |
| 44 | 190 | 6.0 | 86.5 | — | 24.1 | 1.3 | 61.0 |
| 45 | 185 | " | 70.2 | — | 20.0 | 1.1 | 49.2 |
| 46 | 175 | 5.5 | 5.3 | — | 11.4 | 0.2 | 3.7 |
| 47 | " | 5.0 | 52.4 | — | 12.7 | 0.3 | 39.3 |
| 48 | " | 6.5 | 60.1 | — | 14.6 | 0.1 | 45.3 |
| 49 | " | 5.8 | 3.0 | — | 0.8 | 0.1 | 2.0 |
| 50 | " | 5.0 | 77.0 | — | 17.8 | 0.1 | 49.0 |
| 51 | " | " | 35.6 | — | 10.4 | 0.3 | 24.9 |
| 52 | " | 4.5 | 93.3 | — | 18.9 | 1.1 | 63.4 |
| 53 | " | 6.0 | 77.2 | — | 16.8 | 1.1 | 59.3 |
| 54 | " | " | 73.7 | — | 16.3 | 0.9 | 56.5 |
| 55 | " | 5.5 | 81.9 | — | 18.2 | 1.1 | 62.7 |
| 56 | " | 6.0 | 44.8 | — | 12.6 | 0.2 | 32.0 |
| 57 | " | 5.0 | 88.8 | — | 26.7 | 1.0 | 61.1 |
| 58 | " | 5.5 | 8.3 | — | 2.3 | 0.1 | 5.8 |
| 59 | " | 5.0 | 94.3 | — | 26.8 | 0.7 | 66.7 |
| 60 | " | " | 4.3 | — | 0.4 | 0.2 | 0.8 |
| 61 | " | 4.5 | 63.1 | — | 14.6 | 1.0 | 47.6 |
| 62 | 155 | 5.0 | 65.9 | 65.9 | — | — | — |
| 63[12] | " | " | 99.1 | 99.1 | — | — | — |
| 64 | 154 | " | 84.6 | 84.6 | — | — | — |
| 65[12] | 155 | " | 99.4 | 99.4 | — | — | — |
| 66 | " | " | 90.0 | 90.4 | — | — | — |
| 67 | 154 | " | 61.9 | 61.9 | — | — | — |
| 68 | 134 | 5.5 | 78.7 | 78.7 | — | — | — |
| 69 | 174 | 4.0 | 24.8 | — | 13.7 | — | 11.1 |
| 70 | 154 | 5.0 | 11.5 | — | 6.0 | — | 5.5 |
| 71 | 177 | " | 36.4 | — | 17.2 | — | 19.2 |
| 72 | 172 | — | 48.7 | — | 23.3 | — | 25.2 |
| 73 | 232 | 4.7 | 12.7 | — | 1.5 | 0.1 | 11.1 |
| 74 | 192 | 5.0 | 27.6 | — | 6.3 | — | 21.3 |

| Example | Products, % Unidentified by | para/ortho | Material Balance g In | Out | % |
|---|---|---|---|---|---|
| 16 | — | 3.09 | 55.4 | 46.4 | 83.8 |
| 17 | — | 2.49 | 63.8 | 62.8 | 98.4 |
| 18 | 0.2 | 2.73 | 78.6 | 68.6 | 87.3 |
| 19 | — | 2.60 | 59.8 | 57.2 | 95.7 |
| 20 | — | 2.86 | 36.5 | 31.0 | 84.9 |
| 21 | <0.1 | 2.75 | 49.6 | 45.0 | 90.7 |
| 22 | <0.1 | 2.91 | 100.6 | 97.2 | 96.6 |
| 23 | — | 2.43 | 86.3 | 81.6 | 94.6 |
| 24 | — | 2.26 | 70.3 | 70.6 | 100.4 |
| 25 | <0.1 | 2.43 | 79.7 | 74.4 | 93.4 |
| 26 | 0.8 | 2.34 | 68.3 | 58.3 | 85.4 |
| 27 | 0.4 | 2.31 | 53.6 | 44.2 | 82.5 |
| 28 | 0.4 | 2.34 | 147.7 | 136.3 | 92.3 |
| 29 | 0.4 | 2.36 | 100.2 | 90.9 | 90.7 |
| 30 | 0.2 | 2.61 | 78.8 | 75.0 | 95.2 |
| 31 | 0.1 | 2.31 | 69.8 | 68.7 | 98.4 |
| 32 | 0.5 | — | 83.7 | 79.1 | 94.5 |
| 33 | 0.9 | — | 67.7 | 66.7 | 98.5 |
| 34 | — | 2.00 | 114.5 | 114.8 | 100.3 |
| 35 | — | 2.74 | 98.0 | — | — |
| 36 | — | 2.34 | 95.4 | 95.9 | 100.5 |
| 37 | — | 2.37 | 72.6 | 67.5 | 93.0 |
| 38 | — | 2.05 | 84.5 | 64.4 | 76.2 |
| 39 | — | 1.78 | 79.1 | 75.0 | 94.8 |
| 40 | — | 2.03 | 61.3 | 57.9 | 94.5 |
| 41 | — | 2.71 | 75.5 | 56.9 | 75.4 |
| 42 | — | 2.19 | 107.4 | 96.4 | 89.8 |
| 43 | — | 2.31 | 97.9 | 86.3 | 88.2 |
| 44 | — | 2.53 | 64.9 | 50.1 | 77.2 |
| 45 | — | 2.46 | 72.2 | 71.1 | 98.5 |
| 46 | — | 2.64 | 86.9 | 87.3 | 100.5 |
| 47 | — | 3.09 | 76.4 | 67.4 | 88.2 |
| 48 | — | 3.10 | 95.6 | 87.9 | 91.9 |
| 49 | — | 2.50 | 77.5 | 79.4 | 102.5 |
| 50 | — | 2.75 | 42.1 | 38.3 | 91.0 |
| 51 | — | 2.39 | 72.3 | 69.6 | 96.3 |
| 52 | — | 3.35 | 68.7 | 69.0 | 100.4 |
| 53 | — | 3.53 | 86.3 | 86.8 | 100.0 |
| 54 | — | 3.47 | 86.4 | 88.0 | 101.9 |
| 55 | — | 3.45 | 76.8 | 78.0 | 101.6 |
| 56 | — | 2.54 | 83.2 | 76.6 | 92.1 |
| 57 | — | 2.29 | 38.4 | 35.9 | 93.5 |
| 58 | — | 2.52 | 82.1 | 83.1 | 101.2 |
| 59 | <0.1 | 2.49 | 72.7 | 69.7 | 95.9 |
| 60 | 3.0 | 2.00 | 55.0 | 52.6 | 95.6 |
| 61 | — | 3.26 | 67.3 | 64.1 | 95.2 |
| 62 | — | — | 103.1 | 101.6 | 98.5 |
| 63[12] | — | — | 123.2 | 117.0 | 95.0 |
| 64 | — | — | 91.8 | 91.4 | 99.6 |
| 65[12] | — | — | 99.9 | 95.1 | 95.2 |
| 66 | — | — | 95.0 | 93.4 | 98.3 |
| 67 | — | — | 76.1 | 70.3 | 92.4 |
| 68 | — | — | 100.3 | 98.8 | 98.5 |
| 69 | — | 0.81 | 62.0 | 56.5 | 91.1 |
| 70 | — | 0.92 | 68.8 | 59.4 | 86.3 |
| 71 | — | 1.12 | 73.6 | 70.5 | 95.8 |
| 72 | 0.2 | 1.09 | 82.7 | 72.4 | 87.5 |
| 73 | — | 7.40 | 101.9 | 69.9 | 68.6 |

TABLE 3

AROMATIC COMPOUND, R—C₆H₄—R¹

| EXAMPLE | CATALYST NUMBER | R | R¹ | Flow Rate ml/min. | g, moles | Conc. vol. % | Temp. °C. | Carrier Gas[3] Flow Rate ml/min. |
|---|---|---|---|---|---|---|---|---|
| 75 | 14[5] | 1-Cl | 2-Cl | 46.11 | 90.8, 0.62 | 8.1 | 21 | — |
| 76 | 14 | " | " | 40.51 | 79.7, 0.54 | 7.4 | " | — |
| 77 | 14 | " | " | 43.48 | 85.6, 0.58 | 7.1 | " | — |
| 78 | 14 | " | " | 43.26 | 85.2, 0.58 | 5.6 | " | — |

NITRATING AGENT[1]

| EXAMPLE | Flow Rate ml/min. | g, moles | Conc. vol. % | Temp. °C. | Carrier Gas[4] Flow Rate ml/min. | NITRATING AGENT/AROMATIC COMPOUND molar ratio |
|---|---|---|---|---|---|---|
| 75 | 64.57 | 39.8, 0.87 | 11.3 | 10 | 36.5 | 1.40 |
| 76 | 49.23 | 30.3, 0.66 | 9.0 | " | " | 1.22 |
| 77 | 102.42 | 63.1, 1.37 | 16.6 | " | 45.0 | 2.36 |
| 78 | 99.21 | 61.1, 1.33 | 12.5 | " | " | 2.29 |

WATER / REACTION CONDITIONS

| EXAMPLE | Flow Rate ml/min. | g, moles | Conc. vol. % | Temp. °C. | Carrier Gas[3] Flow Rate ml/min. | Temp. °C. | Time Hours | CONVERSION, %[2] |
|---|---|---|---|---|---|---|---|---|
| 75 | 20.16 | 4.9, 0127 | 3.5 | 41 | 405 | 175 | 5.0 | 1.1 |
| 76 | 17.17 | 4.1, 0.23 | 3.1 | 40 | " | 206 | " | 3.0 |
| 77 | 20.78 | 5.0, 0.28 | 3.4 | " | " | 255 | " | 16.2 |
| 78 | 33.27 | 8.0, 0.44 | 4.2 | " | 570 | 281 | " | 29.3 |

PRODUCTS, %

R—C₆H₃(R¹)—NO₂

| | R = R¹ = Cl | | | | MATERIAL BALANCE | | |
|---|---|---|---|---|---|---|---|
| EXAMPLE | 2,3- | 3,4- | By- | 3,4/2,3- | In (g) | Out (g) | % |
| 75 | 0.05 | 0.5 | 0.55 | 10.00 | 135.5 | 123.9 | 91.4 |
| 76 | 0.4 | 2.0 | 0.6 | 5.00 | 114.1 | 110.7 | 97.0 |
| 77 | 2.6 | 11.8 | 1.8 | 4.54 | 153.7 | 146.1 | 95.1 |
| 78 | 3.5 | 19.6 | 6.2 | 5.60 | 154.3 | 148.6 | 96.3 |

[1]Nitrogen dioxide (M.W., 46) unless specified otherwise.
[2]Based on the aromatic compound.
[3]Air
[4]Nitrogen
[5]Catalyst 14 after being employed as the catalyst in Examples 62-72 above, was employed in Examples 75-78 without further treatment with sulfur dioxide and nitrogen dioxide.

| 74 | — | 3.38 | 97.1 | 75.4 | 77.7 |

[1]Nitrogen dioxide (M.W., 46) unless specified otherwise.
[2]Based on the aromatic compound.
[3]Air
[4]Nitrogen
[5]Numbered catalyst precursor prior to treatment for sulfur trioxide uptake. Comparative run to demonstrate the effectiveness of the present invention over prior art catalysts.
[6]Pretreated catalyst for 15 minutes with nitrogen dioxide at operating conditions (for the vapor phase nitration in the absence of the aromatic compound).
[7]Pretreated catalyst as described in Footnote 6 for 12 minutes.
[8]Pretreated catalyst as described in Footnote 6 for 10 minutes.
[9]Pretreated catalyst as described in Footnote 6 for 3 minutes.
[10]No pretreatment.
[11]Catalyst 14 was employed as the catalyst in Examples 62-72 without further treatment with sulfur dioxide and nitrogen dioxide.
[12]Reaction was run at a gauge pressure of 1.03 × 10⁵ pascal (Pa; 15 psig).
[13]Catalyst 15 was employed as the catalyst in Examples 73-74 without further treatment with sulfur dioxide and nitrogen dioxide.

EXAMPLES 75-78

The following examples were run to illustrate the use of the nitration promotion catalyst compositions in the vapor phase nitration of disubstituted aromatic compounds using o- or 1,2-dichlorobenzene as a typical compound.

The reactor system described in Examples 1-15 and the procedure described in Examples 16-74 were employed. The parameters and results are tabulated in Table 3.

Thus, it is apparent that there has been provided, in accordance with the present invention, a process that fully satisfies the objects and advantages set forth hereinabove. While the invention has been described with respect to various specific examples and embodiments thereof, it is understood that the invention is not limited thereto and that many alternatives, modifications, and variations will be apparent to those skilled in the art in light of the foregoing description. Accordingly, it is intended to embrace all such alternatives, modifications, and variations as fall within the spirit and broad scope of the invention.

We claim:

1. In a process for the vapor phase nitration of aromatic compounds where the aromatic compound is contacted with a nitrating agent in the vapor phase to yield the corresponding nitroaromatic compound, the improvement comprising conducting the nitration in the presence of a nitration promoting catalyst which comprises the adduct of:

(a) an alumina-silica-metal oxide combination represented by the formula:

$(Al_2O_3)_a(SiO_2)_b(M_{2/n}O)_c$ wherein M is a metal cation selected from the group consisting of the lanthanides of rare earths, Groups 1b, 2b, 5b, 6b, 7b, and 8 of the Periodic Table of the Elements, and mixtures thereof, and a, b, and c represent weight percent of the $Al_2O_3$, $SiO_2$, and $M_{2/n}O$ components, respectively, in the alumina-silica-metal oxide combination, with a being 0 to 100, b being 0 to 100, and c being 0 to 50, and n represents an integer from 1 to 7 of the valence of the metal cation, with the proviso that the sum of (a+b) must be greater than 0, and (b) a catalytically effective amount of sulfur trioxide.

2. The process improvement in claim 1 wherein the amount of sulfur trioxide is in the range from about 5 weight percent to about 40 weight percent, based on the weight of the alumina-silica-metal oxide combination.

3. The process improvement of claim 1 wherein the alumina-silica-metal oxide combination is selected from the group consisting of crystalline and noncrystalline phases, and mixtures thereof.

4. The process improvement of claim 1 wherein a is 100 and b and c each is 0.

5. The process improvement of claim 1 wherein a and c each is 0 and b is 100.

6. The process improvement of claim 1 wherein a is 9.4, b is 90.6, and c is 0.

7. The process improvement of claim 1 wherein a is 12, b is 87, and c is 0.

8. The process improvement of claim 1 wherein a is 45, b is 53, and c is 0.

9. The process improvement of claim 1 wherein a is 50, b is 50, and c is 0.

10. The process improvement of claim 1 wherein M is a mixture of metal cations.

11. The process improvement of claim 10 wherein M is a mixture of cobalt and molybdenum, with n being, respectively, 2 and 6.

12. The process improvement of claim 11 wherein a is 86.5, b is 0, and c is 13.5.

13. The process improvement of claim 12 wherein c comprises 3.5 weight percent cobalt (II) oxide and 10 weight percent molybdenum (VI) oxide.

14. The process improvement of claim 12 wherein a is 80.5, b is 0, and c is 19.5.

15. The process improvement of claim 14 wherein c comprises 4.5 weight percent cobalt (II) oxide and 15 weight percent molybdenum (VI) oxide.

16. The process improvement of claim 10 wherein M is a mixture of nickel and tungsten, with n being, respectively, 2 and 6.

17. The process improvement of claim 16 wherein a is 17.4, b is 65, c is 17.6.

18. The process improvement of claim 17 wherein c comprises 3.3 weight percent nickel (II) oxide and 14.3 weight percent tungsten (VI) oxide.

19. The process improvement of claim 10 wherein M is cobalt, with n being 2 and 3.

20. The process improvement of claim 19 wherein a is 0, b is 83.7, and c is 16.3.

21. The process improvement of claim 1 wherein the nitrating agent is nitrogen dioxide.

22. The process improvement of claim 1 wherein the nitrating agent is admixed with a carrier gas prior to reaction with the aromatic compound.

23. The process improvement of claim 22 wherein the carrier gas is nitrogen.

24. The process improvement of claim 1 wherein the nitration promoting catalyst is conditioned by pretreatment with the nitrating agent.

25. The process improvement of claim 24 wherein the pretreatment is carried out for about 1 minute to about 1 hour.

26. The process improvement of claim 1 wherein the aromatic compound is an aromatic hydrocarbon.

27. The process improvement of claim 26 wherein the aromatic hydrocarbon is selected from the group consisting of benzene and toluene.

28. The process improvement of claim 1 wherein the aromatic compound is a haloaromatic compound.

29. The process improvement of claim 28 wherein the haloaromatic compound is selected from the group consisting of chlorobenzene, bromobenzene, iodobenzene, and o-dichlorobenzene.

30. The process improvement of claim 1 wherein the aromatic compound is an aromatic ether.

31. The process improvement of claim 30 wherein the aromatic ether is selected from anisole and phenetole.

32. The process improvement of claim 1 wherein the aromatic compound is an aromatic carboxylate.

33. The process improvement of claim 2 wherein the aromatic carboxylate is selected from the group consisting of benzoic acid, methyl benzoate, and ethyl benzoate.

34. The process improvement of claim 1 wherein the concentration of the aromatic compound in the feed mixture is between about 1 percent and about 15 percent by volume.

35. The process improvement of claim 1 wherein about 0.5 to about 5 moles of nitrating agent are used per mole of aromatic compound.

36. The process improvement of claim 1 wherein the aromatic compound is admixed with a carrier gas prior to reaction with the nitrating agent.

37. The process improvement of claim 6 wherein the carrier gas is an oxygen-containing gas.

38. The process improvement of claim 7 wherein the oxygen-containing gas is air.

39. The process improvement of claim 1 wherein water vapor is admixed with the feed mixture prior to reaction between the aromatic compound and the nitrating agent.

40. The process improvement of claim 9 wherein the water vapor is present in the feed mixture in a concentration ranging from about 0.1 percent to about 15 percent by volume.

41. The process improvement of claim 1 wherein the vapor phase reaction is carried out at temperatures ranging from about 80° C. to about 300° C.

42. The process improvement of claim 41 wherein the temperature ranges from about 150° C. to about 250° C.

43. The process improvement of claim 1 wherein the aromatic compound is a monosubstituted aromatic compound having an ortho-para orientation substituent and the nitroaromatic compound is a mixture of ortho, meta, and para isomers.

44. The process improvement of claim 43 wherein the monosubstituted aromatic compound is chlorobenzene and the nitroaromatic compound is a mixture of o-, m-, and p-nitrochlorobenzene.

45. The process improvement of claim 44 wherein the para/ortho isomer ratio is about 1.8–3.5/1.

* * * * *

UNITED STATES PATENT AND TRADEMARK OFFICE
CERTIFICATE OF CORRECTION

PATENT NO. : 4,415,744

DATED : November 15, 1983

INVENTOR(S) : IGNATIUS SCHUMACHER, KANG-BO WANG

It is certified that error appears in the above-identified patent and that said Letters Patent is hereby corrected as shown below:

Column 13, after line 51, add --[34] After one vapor phase nitration run on virgin alumina-silica-metal oxide combination material (catalyst precursor) for comparative purposes (Example 60), the catalyst was prepared.--

Column 13, line 56, delete "5" and substitute therefor --15--.

Column 16, line 24, Example 55 (in Table 2) under the heading "Flow Rate, ml/min.", delete "55.27" and substitute therefor --52.27--.

Column 16, line 53, Example 23 (in Table 2) under the heading "g, moles", delete "0.55" and substitute therefor --0.22--.

Column 17, line 20, Example 65 (in Table 2) under the heading "g, moles", delete "0.29" and substitute therefor --0.26--.

Column 17, line 23, Example 68 (in Table 2) under the heading "Temp., °C", delete "50" and substitute therefor --40--.

Column 17, line 47, Example 31 (in Table 2) under the heading "Time, Hours", delete "50" and substitute therefor --5.0--.

Column 17, line 53, Example 39 (in Table 2) under the heading "ortho", delete "35.8" and substitute therefor --25.8--.

Column 22, line 40, Claim 37, delete "6" and substitute therefor --36--.

UNITED STATES PATENT AND TRADEMARK OFFICE
CERTIFICATE OF CORRECTION

PATENT NO. : 4,415,744

DATED : November 15, 1983

INVENTOR(S) : IGNATIUS SCHUMACHER, KANG-BO WANG

It is certified that error appears in the above-identified patent and that said Letters Patent is hereby corrected as shown below:

Column 22, line 42, Claim 38, delete "7" and substitute therefor --37--.

Column 22, line 48, Claim 40, delete "9" and substitute therefor --39--.

Signed and Sealed this

Fourteenth Day of August 1984

[SEAL]

Attest:

GERALD J. MOSSINGHOFF

Attesting Officer

Commissioner of Patents and Trademarks